United States Patent [19]

Hamon et al.

[11] Patent Number: 4,772,707
[45] Date of Patent: Sep. 20, 1988

[54] CERTAIN N,N'-DIPYRIDINE COPPER OR MANGANESE COMPLEXES

[75] Inventors: Jean-René Hamon, Rennes; Claude J. Lapinte, Cesson Sevigne, both of France

[73] Assignee: Centre Natinal de la Recherche Scientifique, Paris, France

[21] Appl. No.: 868,392

[22] Filed: May 28, 1986

[30] Foreign Application Priority Data

May 30, 1985 [FR] France ............................ 85 08109

[51] Int. Cl.$^4$ ......................... C07F 1/08; C07F 13/00
[52] U.S. Cl. ........................................ 546/2; 546/8; 546/9; 546/10; 436/136; 436/138
[58] Field of Search .............................. 546/2, 10, 9, 8

[56] References Cited

PUBLICATIONS

Chemical Abstracts, vol. 94, 1981, p. 693, No. 57318E.
Crumbliss, A. L., Gestaut L. J., J. Coord. Chem., 1976, vol. 5, pp. 109–111.
Kitagawa, S., Munakata, M., Inorg. Chem., 1981., vol. 20, No. 7, pp. 2261–2267.

*Primary Examiner*—Alan L. Rotman
*Attorney, Agent, or Firm*—Fulbright & Jaworski

[57] ABSTRACT

The present invention relates to compositions useful for the detection of oxygen in a humid medium, characterized in that they comprise at least one complex of the formula $(LMX)_n$ in which the ligand L is selected from among the groups:

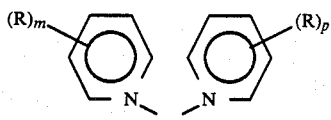

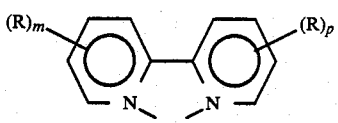

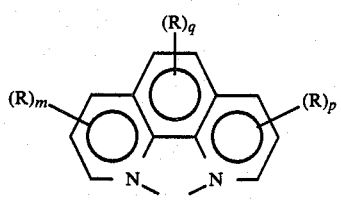

where:
R represents $Cl, Br, NO_2, C_{1-4}$-alkoxyl, $C_{1-4}$-alkyl,
m and p are comprised between 0 and 3,
q is comprised between 0 and 2,
the substituent R on the pyridine nuclei never occupying a position neighboring the nitrogen atom,
$X = Cl, Br, I, NO_3, ClO_4$,
M represents Cu or Mn, and
n is equal to 1 or 2, as colored indicator of the presence of oxygen in a humid medium, in solution in an acceptable solvent.

The present invention also relates to a process for preparing such compositions, and detectors of the presence of oxygen comprising them.

2 Claims, No Drawings

CERTAIN N,N'-DIPYRIDINE COPPER OR MANGANESE COMPLEXES

The present invention relates to colored indicators of the presence of oxygen in a moist medium, compositions useful for the detection of the presence of oxygen comprising them, as well as the process for the preparation of these compositions and of detectors of the presence of oxygen.

The present invention was made in the Laboratoire de Chimie des Organometalliques of the University of Rennes I, a unit associated with the Centre National de la Recherche Scientifique n° 415.

Many substances must be preserved shielded from oxygen and often in a humid medium. In particular, chemical substances, such as paints, varnishes, glues, pharmaceutical products, or agricultural-food products, are currently packaged under vacuum or under an inert atmosphere since the presence of oxygen causes deterioration in them.

The detection of defects in such vacuum or inert gas packages, that is to say the detection of the presence of oxygen inside the packages is a delicate problem. In fact, to establish the contamination by oxygen of the package protecting the products, two means are known at present. The first consists of making a sampling of the stock to test the quality of the product by taking a specimen. This solution involves the opening of the packaging and hence the degradation of the sample. Another means consists, for transparent wrappings, of observing directly the deterioration, with the drawback that the latter only appears clearly when the contamination by oxygen is already well advanced.

The present invention proposes a means for detecting very rapidly the presence of oxygen in a packaging, even in a humid medium, by means of a colored indicator which changes in color on contact with oxygen, even in very small amount.

The present invention relates to compositions useful for detecting the presence of oxygen in a humid medium comprising at least one complex of the general formula $$(LMX)_n \quad (I)$$

in which the ligand L is selected from among the groups:

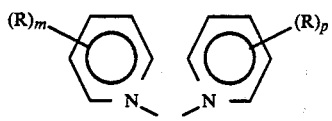

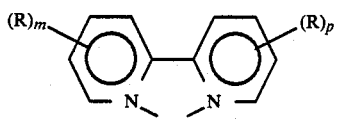

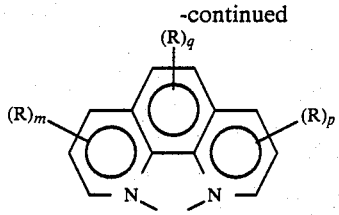

where:
R represents $Cl, Br, NO_2, C_{1-4}$-alkoxyl, $C_{1-4}$-alkyl,
m and p are comprised between 0 and 3,
q is comprised between 0 and 2, the substituent R on the pyridine nuclei never occupying a neighboring position to the nitrogen atom,
$X = Cl, Br, I, NO_3, ClO_4$,
M represents Cu or Mn, and
n is equal to 1 or 2,
as colored indicator of the presence of oxygen in a moist medium, in solution in an acceptable solvent.

In the general formula I, the linkage M-X represents either a covalent bond, or an ionic bond, according to the nature of the anion.

In the solid state, these compounds generally exist in dimeric form (n=2). In dilute solution, it is in the form of a monomer (n=1) that they react with the oxygen.

Among the compounds of formula 1, there are used particularly as colored indicator of the presence of oxygen in a human medium, the complexes of formulae:

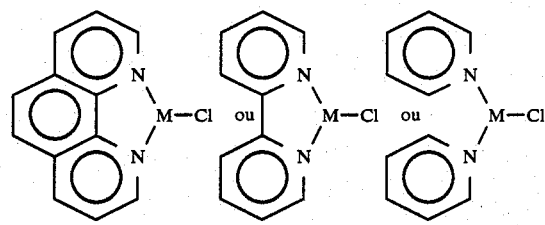

where M represents Cu or Mn.

In solution, in general in monomeric form, these organometallic complexes of transition metals in reduced form have the property of being oxidized with a complete change in color in the presence of oxygen. The reaction with the oxygen is rapid in spite of the unfavorable redox potential values (more than 0.5 V). Due to the fact of their relatively low redox potential (about +0.200 V/ECS in methanol) these complexes do not react with water. This is why these organometallic complexes may be used to detect the presence of oxygen, even in a moist medium.

Thus, in the case of the complex 1-10 phenanthroline-CuCl, the orange complex in the absence of oxygen becomes blue-green on contact with oxygen, and its color does not change in the presence of water.

The electronic effect which results from the substitution of the ligands modifies the speed of the oxidation reactions in particular and may be used to modulate the sensitivity of the detector. However, substitution at a position neighboring the nitrogen slows down the oxidation reactions considerably.

These organometallic complexes have the advantage of being relatively stable in solution shielded from oxygen, their dismutation being fairly slow. Moreover, the addition of multitoothed ligands, like polypeptides, contributes to augmenting the stability of these complexes in solution.

To augment the stability of the complexes in solution, by isolating the complex from the water by hydrophobic effect around the complex, it is hence possible to add to the solution a jelling agent like a polypeptide such as gelatine, in proportions of 1 to 10 % in the composition, a short polypeptide and/or a surface active agent, such as lauryl-sulfate, at miscellaneous concentrations, for example $10^{-2}$ mol. for lauryl sulfate.

Thus, for example, in the presence of food gelatine stability of the orange complex 1,10 phananthroline-CuCl is of the order of one year at a temperature of about 10° C.

As natural jelling agent it is therefore possible to use gelatine, but it is also possible to use gums such as gum arabic or gum tragacanth. It is possible also to use synthetic jelling agents.

The solvents particularly adapted to the invention are lower aliphatic alcohols, acetone and their mixtures with water. In particular, for the complex 1,10 phenanthroline-CuCl, it is ethanol, acetone, or water/ethanol or water/acetone mixture which are preferably used. The response speed of these compositions, useful for detecting the presence of oxygen varies according to the value of the proportion water/acetone or water/alcohol of the mixture. Preferably mixtures comprising about 70 to 90% of water are used.

The colors of the reduced and oxidized forms depend on the metal-ligand couple and the rigidity of the ligand. Thus, the bipyridyl -CuCl and 1,10-phenanthroline-CuCl complexes are orange and become bluegreen after oxidation whereas the complex (pyridine)$_2$ -CuCl of pale yellow color becomes blue. The density of the color as well as the sensitivity of these compositions depend on the concentration of colored indicator. In particular molar concentrations comprised between $10^{-3}$ and $10^{-2}$ are preferred.

In a particular embodiment of the invention, the composition useful for detecting the presence of oxygen has a jell structure, a mixture of a solution of the colored indicator in an acceptable solvent and a support in gel form, for example food gelatine. This structure is particularly adapted to the subsequent use of these compositions, as will be seen from the following.

The present invention also relates to a process for the preparation of a composition useful for detecting the presence of oxygen, characterized by carrying out:

(a) the placing in solution of a complex colored indicator of the presence of oxygen in a humid medium such as defined previously in an acceptable solvent, such as a lower aliphatic alcohol or acetone, in a medium free of oxygen, and as the case may require (b) the addition, in an oxygen-free medium, of the solution to a gel, to obtain a composition according to the invention.

The examples describe the preparation of certain useful complexes according to the invention. The complexes with manganese are produced and employed in a similar manner.

To prepare the compositions according to the invention, the complex prepared is dissolved under an oxygen-free atmosphere in acetone or ethanol. The solution obtained can then be added to a solution of a jelling agent, still under an oxygen-free atmosphere, to obtain a final solution containing 70 to 90% of water. As an example of a jelling agent, may be mentioned particularly food gelatine, although other natural or synthetic agents are utilizable.

There is hence available a gel in which the colored indicator is incorporated. This structure permits not only the detection qualitatively of the presence of oxygen, by change in color of the gel, but also the estimation quantitatively of the oxygen present to the extent that, the diffusion of the oxygen being progressive in the gel-form structure, the change in color progresses also in the gelled structure.

It it is desired simply to detect qualitatively the presence of oxygen in a controlled enclosure, it is possible to use as detector of the presence of oxygen a support incorporating the colored indicator according to the invention or a composition according to the invention. The present invention relates therefore to a detector of the presence of oxygen comprising a composition according to the invention incorporated in a porous support. This detector is introduced into the package at the time of packaging under vacuum or under inert gas.

It is also possible to use as detector any container filled with a composition according to the invention in the form of solution or of gel, allowing the change in color to appear and of which one of the walls is permeable to oxygen, for example, a transparent container whose opening is closed by a gas permeable membrane, or a capillary tube filled with gel, or a transparent container permeable to oxygen, or a self-destructible bulb filled under an inert atmosphere with composition according to the invention, which is broken at the time of the test.

In the case where it is desired not only to check the presence of oxygen, but also the amount of oxygen present in the packaging, or the progress of contamination by oxygen, it will be preferable to use as detector or a container of oblong shape, like a tube of glass or of plastic material filled with a composition according to the invention in gel form. One of the ends is if necessary obturated by a membrane permeable to the gas, for example a film of polystyrene or of polyethylene comparable to the plastic films used for the preservation of foodstuffs. This fine membrane offers the advantage of preventing the drying out of the detector and of separating it from the packaged product.

To produce these detectors, small glass or plastics tubes are filled under an inert atmosphere with the food gelatine in an aqueous medium previously supplemented with an alcoholic or acetonic solution of the colored indicator, at a temperature of about 50° C. After cooling, the tubes are closed with a gas permeable plastics film.

In the presence of oxygen, the gel changes in color from the surface protected by the permeable membrane. The speed of advance of the oxygen into the detector, which determines the change in color of the gel, is of the order of some mm per hour. This speed may be reduced or increased by modifying the ratio water/alcohol or water/acetone of the composition, the concentration of indicator, the thickness of the membrane and the density of the gel. The sensitivity of the detector depends also on these factors. The detectors according to the invention have a sensitivity threshold of the order of $10^{-6}$ mole of oxygen.

It is also possible to employ transparent tubes by the meter, cut off at the time of placing in position, of which the welds are permeable and/or porous to the gas, or tubes themselves permeable and/or porous to the gas.

These detectors are placed in the packages at the time of the packaging. They are useful, particularly in packages of food products, but in general in any container with a controlled atmosphere.

In the case of detectors in the form of a vessel containing a composition comprising gelatine, placed in packagings to be preserved shielded from heat, these detectors can also contribute to detecting the interruption of the cold storage history. In fact, at a temperature above 30° C., the composition again becomes fluid in the container; by the resumption of cold storage, the composition again becomes solid in a form different from its initial form in the container. The color of the indicator renders this change in form and hence the interruption of the cold storage history, perceptible.

According to a modification, it is possible to use cross-linked gelatine, insensitive to temperature differences or to add to the compositions a cross-linking agent maintaining the gel structure even at higher temperatures, of the order of 50° to 70°, for example.

Other advantages and features of the present invention will appear from reading the following examples.

EXAMPLE 1

Preparation of Cu(I)Cl

CuCl is prepared by the reduction of $CuCl_2$, $2H_2O$ (Prolabo) with ascorbic acid (Merck) or by purification of commercial Cu(I)Cl according to the literature (Andrieth L. F., Bailar J. C., Ferneluis W. C., Johnson W. C., Kork R. E., Inorg, Synth., 1946, 2,1).

EXAMPLE 2

Preparation of the complex 1-10 pheanthroline Cu(I)Cl

To a suspension of 1.98 g (20 mmoles) of CuCl in 50 ml of $CH_2Cl_2$ stirred vigorously, is added drop by drop, by means of a dropping funnel, and under an inert atmosphere (argon or nitrogen) a solution of 3.96 g (20 mmoles) of 1-10 phenanthroline (Janssen) in 50 ml of $CH_2Cl_2$. At the end of the addition, the solution is of very deep orange color. This solution is then filtered through a canula under argon, concentrated under vacuum to a volume of 10 ml and the addition of 100 ml of pentane precipitates quantitatively 5.58 g (20 mmoles) of complex 1-10 phananthroline Cu(I)Cl (orange-brown), isolated by filtration under an inert atmosphere and dried under vacuum ($10^{-2}$ mm Hg for two hours).

The production can also be done in a single step starting from a cuprous ion source $[Cu(CH_3CN)_4ClO_4]$ to which the phenanthroline is added in situ (Crumbliss A. L., Gestaut L. J., J. Coord. Chem., 1976, 5, 109-111).

EXAMPLE 3

Oxygen detecting colored indicator 0.11 g of the complex 1-10 phananthroline Cu(I)Cl, prepared by the method described above, are dissolved at 20° C. in 8 ml of $C_2H_5OH$ and transferred by canula under an inert atmosphere into 31 ml of an aqueous solution (distilled water) of 3 g of food gelatine (Prolabo) kept at 50° C. This orange solution ($10^{-2}$ M) is then transferred under argon into self-breakable bulbs of 8 mm diameter and sealed under vacuum after freezing to −196° C. These samples, ready for use, are preserved in the refrigerator. If a bulb is opened to the air, the progressive diffusion of the oxygen is seen due to the change in color caused by the oxidation of the 1-10 phenanthroline Cu(I)Cl complex of orange color, into an oxidized complex [1-10 phenanthroline Cu(II)-ClOH]$_2$ of turquoise color.

EXAMPLE 4

Preparation of the complex 2-2' bipyridyl Cu(I)Cl

To a suspension of 1.98 g (20 mmoles) of CuCl in 50 ml of $CH_2Cl_2$ at 20° C., stirred vigorously, is added drop by drop by means of a bromine funnel and under an inert atmosphere (argon or nitrogen), a solution of 3.12 g (20 mmoles) of 2-2' bipyridyl (Fluka) in 50 ml of $CH_2Cl_2$. At the end of the addition, the solution is very deep orange color. This solution is then filtered through a canula under argon, concentrated under vacuum to a volume of 10 ml and the addition of pentane precipitates quantitatively 5.10 g (20 mmoles) of the complex 2-2' bipyridyl Cu(I)Cl (orange-brown) isolated by filtration under an inert atmosphere and dried under vacuum ($10^{-2}$ mm Hg for 2 hours). Kitagawa S; and Manakata M. prepare this compound by a similar method (Inorg. Chem., 1981, 20, 2261-2267).

EXAMPLE 5

Oxygen detecting colored indicator 0.24 g of the complex 2,2' bipyridyl Cu(I)Cl, prepared by the method described above, are dissolved at 20° C. in 10 ml of $CH_3COCH_3$ and transferred through a canula under an inert atmosphere into 70 ml of aqueous solution (distilled water) of 5.25 g of food gelatine (Prolabo) kept at 50° C. This orange solution ($10^{-2}$ M) is then transferred under argon into self-breakable ampules of 8 mm diameter and sealed under vacuum.

These ready-to-use specimens are preserved in the refrigerator. If an ampule is opened to air, the progressive diffusion of the oxygen is observed due to the change in color caused by the oxidation of the complex 2,2' bipyridyl Cu(I)Cl of orange color ($\lambda$max: 417.520 nm) into the oxidized complex [2,2' bipyridyl Cu (II)-ClOH]$_2$ of turquoise color ($\lambda$max: 632 nm).

EXAMPLE 6

Detection of the oxygen of the air

The indicator prepared according to examples 4 and 5 enables the determination of the time of exposure to oxygen of the air by measurement of the height of gel which has turned turquoise.

| Time of exposure to air | Height of gel which has turned turquoise |
|---|---|
| 15 minutes | discolored meniscus |
| 1 hour | 1 mm |
| 24 hours | 7-8 mm |
| 48 hours | 13-15 mm |
| 72 hours | 20-22 mm |

Remark:

In certain cases, before the appearance of the turquoise color, an intermediate pale grey color is observed.

EXAMPLE 7

Preparation of the complex (pyridine)$_2$Cu(I)Cl

To a suspension of 1.98 g (20 mmoles) of CuCl in 50 ml of $CH_2Cl_2$ at 20° C., stirred vigorously, is added drop by drop, by means of a dropping funnel and under an inert atmosphere (argon or nitrogen), a solution of 3.23 ml (40 mmoles) of pyridine in 50 ml of $CH_2CL_2$. At the end of the addition, the solution is a pale green color. This solution is then filtered through a canula under argon, concentrated under vacuum to a volume of 10 ml and the addition of pentane precipitates 2.5 g of complex (pyridine)$_2$ Cu(I)Cl (pale green; unoptimized yield, about 50 %) isolated by filtration under an inert atmosphere and dried under vacuum ($10^{-2}$ mm Hg for 2 hours).

EXAMPLE 8

Oxygen detector colored indicator 0.154 g of the complex (pyridine)$_2$ Cu(I)Cl, prepared by the method described above, are dissolved at 20° C. in 7.5 ml of C$_2$H$_5$OH and transferred through a canula under an inert atmosphere into 52 ml of aqueous solution (distilled water) of 3.75 g of food gelatin (Prolabo) maintained at 50° C. This ecru colored solution (gelatin color) ($10^{-2}$ M) is then transferred under argon into self-breakable bulbs of 8 mm diameter and sealed under vacuum after freezing to $-196°$ C. These read-to-use specimens, are preserved in a refrigerator. If a bulb is opened to air, the progressive diffusion of the oxygen is observed due to the change in color caused by the oxidation of the complex (pyridine)$_2$Cu(I)Cl of ecru color into an oxidized complex [(pyridine)$_2$Cu(II)ClOH]$_2$ of ocean-blue color.

We claim:

1. A compound of the formula $$(LMX)_n \qquad (I)$$

in which the ligand L is selected from the group consisting of

where:
R represents Cl, Br, NO$_2$, C$_{1-4}$-alkoxyl, C$_{1-4}$-alkyl,
m and p are in the range from about 0 and 3, and wherein
R on the pyridine nuclei and the nitrogen atom occupy non-adjacent positions,
X represents Cl, Br, I, NO$_3$, ClO$_4$,
M represents Cu or Mn, and
n is equal to 1 or 2.

2. The compound of claim 1, wherein said complex is:

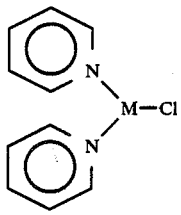

where M represents Cu or Mn.

* * * * *

UNITED STATES PATENT OFFICE
CERTIFICATE OF CORRECTION

Patent No. 4,772,707    Dated September 20, 1988

Inventor(s) Jean-René Hamon, Claude J. Lapinte

It is certified that error appears in the above-identified patent and that said Letters Patent is hereby corrected as shown below:

Column 3, line 13, kindly delete "phananthroline-" and insert instead --phenanthroline- --.

Column 4, line 11, kindly delete "It" and insert instead --If--.

Column 4, line 36, kindly delete "or".

Column 5, line 45, kindly delete "phananthroline" and insert instead --phenanthroline--.

Column 5, line 56, kindly delete "phananthroline" and insert instead --phenanthroline--.

Column 6, line 19, kindly delete "Manakata" and insert instead --Munakata--.

Column 7, line 21, kindly delete "read-to-use" and insert instead --ready-to-use".

Signed and Sealed this

Eleventh Day of July, 1989

Attest:

DONALD J. QUIGG

Attesting Officer    Commissioner of Patents and Trademarks